United States Patent
Berry et al.

(10) Patent No.: US 10,299,843 B2
(45) Date of Patent: May 28, 2019

(54) TULIP HEAD AND COLLET FOR A POLY AXIAL SCREW

(71) Applicants: Bret Michael Berry, Tallahassee, FL (US); Jeremy S. Alsup, Bountiful, UT (US)

(72) Inventors: Bret Michael Berry, Tallahassee, FL (US); Jeremy S. Alsup, Bountiful, UT (US)

(*) Notice: Subject to any disclaimer, the term of this patent is extended or adjusted under 35 U.S.C. 154(b) by 25 days.

(21) Appl. No.: 15/612,222

(22) Filed: Jun. 2, 2017

(65) Prior Publication Data

US 2018/0344357 A1  Dec. 6, 2018

(51) Int. Cl.
*A61B 17/70* (2006.01)
*A61B 17/88* (2006.01)
*A61B 17/86* (2006.01)

(52) U.S. Cl.
CPC ...... *A61B 17/8605* (2013.01); *A61B 17/7035* (2013.01); *A61B 17/7076* (2013.01)

(58) Field of Classification Search
CPC ............ A61B 17/7032; A61B 17/7037; A61B 17/8605; A61B 2017/00526
USPC ........................................ 606/266, 267, 270
See application file for complete search history.

(56) References Cited

U.S. PATENT DOCUMENTS

| | | | | |
|---|---|---|---|---|
| 6,063,090 A * | 5/2000 | Schlapfer | ............ | A61B 17/7037 606/270 |
| 8,328,817 B2 * | 12/2012 | Strauss | .............. | A61B 17/7032 606/102 |
| 8,628,558 B2 * | 1/2014 | Harvey | .............. | A61B 17/7032 606/267 |
| 8,696,717 B2 * | 4/2014 | Rock | .................. | A61B 17/7037 606/266 |
| 8,814,919 B2 * | 8/2014 | Barrus | ............... | A61B 17/7037 606/266 |
| 2010/0152787 A1 * | 6/2010 | Walsh | ................ | A61B 17/7037 606/308 |
| 2011/0270325 A1 * | 11/2011 | Keyer | ................ | A61B 17/7007 606/305 |
| 2015/0148848 A1 * | 5/2015 | Doubler | ............... | A61B 17/704 606/278 |
| 2016/0045228 A1 * | 2/2016 | Biedermann | ...... | A61B 17/7032 606/266 |
| 2017/0086885 A1 * | 3/2017 | Duncan | .............. | A61B 17/7032 |

* cited by examiner

*Primary Examiner* — Pedro Philogene
*Assistant Examiner* — David C Comstock
(74) *Attorney, Agent, or Firm* — James M. Smedley LLC; James M. Smedley, Esq.

(57) ABSTRACT

The present invention generally relates to connectors that connect bone screws with fusion rods for use in stabilizing surgery such as spinal fusion surgery, and to bone screw systems comprising such connectors. In particular, the present invention relates to poly axial screw systems configured to provide a stable but adjustable angular placement. Furthermore, embodiments of the present invention relate to tulip connectors which have a head and a collet, that are configured to rotatably and pivotably lock onto the ball head of a poly axial screw shaft into a manually adjustable locked position, to methods achieving this locked position with or without using a tulip assembly tool, and to the tulip assembly tool that has outer hooks to grab the tulip head and a center dowel to push the collet down into the locked position.

18 Claims, 3 Drawing Sheets

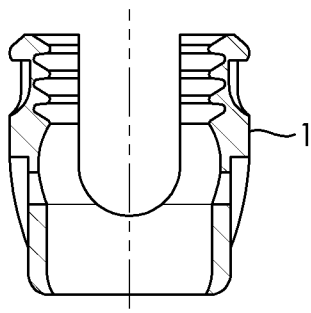
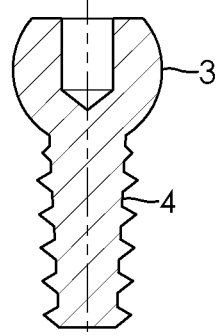
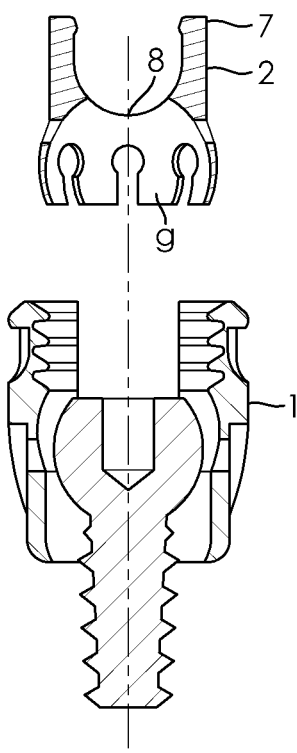
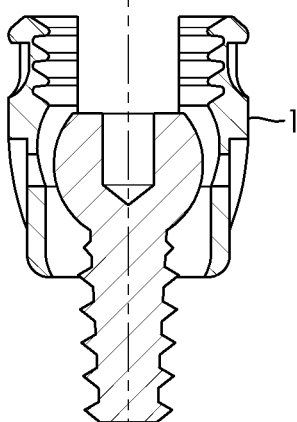
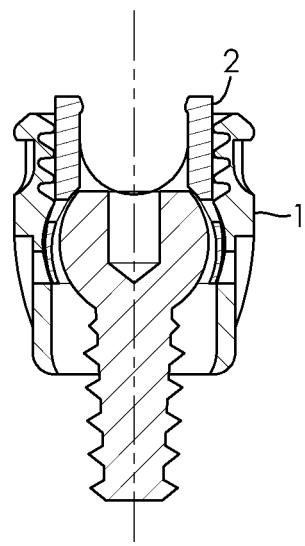
FIG. 3      FIG. 4      FIG. 5
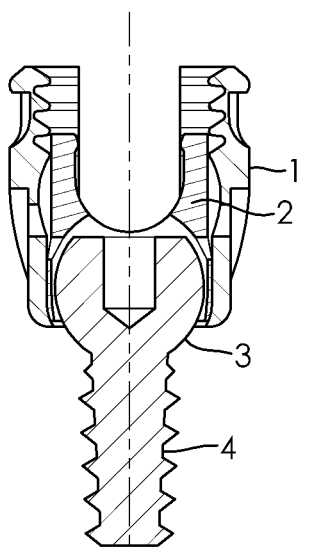
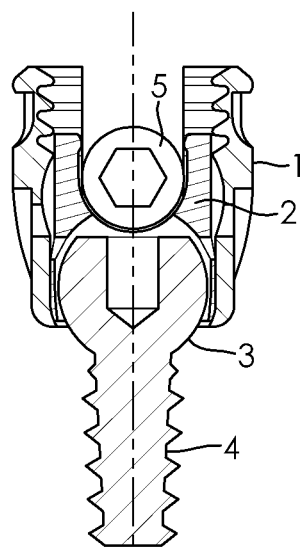
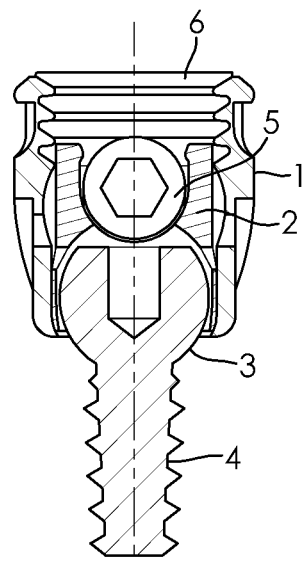
FIG. 6      FIG. 7      FIG. 8

TULIP HEAD AND COLLET FOR A POLY AXIAL SCREW

FIELD OF THE INVENTION

The present invention generally relates to connectors that connect bone screws with fusion rods for use in stabilizing surgery such as spinal fusion surgery, and to bone screw systems comprising such connectors. In particular, the present invention relates to poly axial screw systems configured to provide a stable but adjustable angular placement. Furthermore, embodiments of the present invention relate to tulip connectors which have a head and a collet, that are configured to rotatably and pivotably lock onto the ball head of a poly axial screw shaft into a manually adjustable locked position, to methods achieving this locked position with or without using a tulip assembly tool, and to the tulip assembly tool that has outer hooks to grab the tulip head and a center dowel to push the collet down into the locked position.

BACKGROUND OF THE INVENTION

Poly axial screws are used e.g. for fixation of a patient's spinal column in spinal surgery that is performed to fuse individual spinal vertebrae. A screw shaft is inserted into the bone, e.g. the pedicle of each vertebrae to be fused, and a fusion rod is attached by connectors mounted on the screw shaft to multiple screws, to form a supporting structure that fixates the vertebrae and prevents movement. Over time, lack of movement as well as bone transplants implanted at the surgery site for this purpose allows bone to grow and permanently fuse the bones of the vertebrae after surgery.

Many different models exist for pedicle screws which generally have a screw shaft and a U-shaped connector that connects the screw to a fusion rod. In mono axial screws, the head of the screw can be aligned with the position of the rod only to a limited extent, necessitating complicated bending to correct the angle. Poly axial screws generally have a screw shaft with ball head and the U-shaped connector or tulip rotatably and pivotably coupled thereto.

While poly axial screws allow more flexibility in positioning of the screw shafts and fusion rods, they often lack the rigidity or stability required to achieve and maintain an accurate angular placement during surgery, may be difficult to connect to a fusion rod, and/or create even more bulky structures that interfere with surgery, causing more tissue damage and/or require larger incisions.

Typically, the parts of a poly axial screw are configured for pre-assembly before implantation, the shape, size or number of their parts making them complicated to assemble, bulky, and/or are difficult to implant. The resulting system may lack flexibility or rigidity or both. The bulk of the poly axial screw system can also complicate surgery before and after implanting of the screws, as it may require larger or different incisions and more soft tissue may have to be removed, thus complicating surgery and prolonging healing times. Also the bulky structure, once implanted, may interfere with the view of the surgeon during the ongoing surgery, e.g. during placement of bone implants, and also if discs (between the vertebrae) are removed and replaced with interbodies, as is often the case (e.g. herniated discs). Further the bulk may interfere with imaging techniques to determine correct placement of the screw system itself, or of the placement of related therapeutic components, such as interbody transplants and positioning tools.

In some systems, threaded nuts are used to secure the rods to the connectors. The rods can be provisionally held in position by loosely tightening the nuts, and after desired adjustments are made, the nuts can be further tightened by torque and fixated into a final position. Such procedures typically requires a torque wrench or similar device, and to prevent torque from being transferred to the patient, require an anti-torque device in parallel. The effective use of both devices requires skill and is dependent upon the strength and experience of the surgeon. The provisionally loosely tightening typically results in unpredictable inconsistent results with regards to adjustability—the nut may have been tightened to little, resulting in the correct position being lost, e.g. as the structure shifts in the course of the ongoing surgery as the structure or the surrounding bone and tissue is manipulated, or the nut may have been tightened too much, so adjustments cannot be made without first loosening it again, applying unnecessary torque or requiring use of an anti-torque device.

Therefore, there is a need in the art for a poly axial screw system that avoids bulk, is easily and quickly assembled, has flexible assembly options, is easily positioned, provides a sufficient and consistent degree of rigidity to retain its preliminary axial position after assembly, and is easily and quickly adjusted before fixation into the final position. Also, there is a need in the art for a system that avoids torque, in particular when adjusting repeatedly before fixation. These and other features and advantages of the present invention will be explained and become apparent to one skilled in the art through the following description of the invention.

SUMMARY OF THE INVENTION

The present invention generally relates to connectors that connect bone screws with fusion rods for use in stabilizing surgery such as spinal fusion surgery, and to bone screw systems comprising such connectors. In particular, the present invention relates to poly axial screw systems configured to provide a stable but adjustable angular placement. Furthermore, embodiments of the present invention relate to tulip connectors which have a head and a collet, that are configured to rotatably and pivotably lock onto the ball head of a poly axial screw shaft into a manually adjustable locked position, to methods achieving this locked position with or without using a tulip assembly tool, and to the tulip assembly tool that has outer hooks to grab the tulip head and a center dowel to push the collet down into the locked position.

According to an embodiment of the present invention, provided is a tulip for connecting a fusion rod to a poly axial screw, the tulip comprising a head and a collet configured for assembly onto a ball head of a poly axial screw shaft during spinal fusion surgery; wherein the collet is configured with an upper saddle part with a base and two saddle horns and a lower jaw joint part; wherein the saddle, its base and its two saddle horns are configured to connect to a fusion rod, with the length of the rod sitting across the saddle base, the two horns cradling part of the sides of the rod; wherein the jaw joint is configured with an open and a closed position, and comprises a plurality of jaw joint members that are configured to be separated in the open position, and to make closer contact with each other in the closed position, and the jaw joint in its open position is configured to accept and fit loosely around the ball head of a poly axial screw shaft, and in its closed position is configured to tightly fit around the ball head; wherein the tulip head comprises two chambers, an upper chamber and a lower chamber; wherein the upper chamber is wider than the lower chamber, and the upper chamber is configured to loosely fit the ball head of the poly axial screw shaft and the collet with its jaw joint in the open position; wherein the lower chamber is tighter than the upper chamber and the lower chamber is configured to tightly fit the collet with its jaw joint in a closed position around the ball head of the poly axial screw shaft, and thus to lock the tulip in position while allowing it to rotate and pivot against the ball head upon actuation of manual force; wherein the top part of the tulip head is configured to engage with a fastener, thus allowing fixation of the poly axial screw to the fusion rod in their final positions.

According to an embodiment of the present invention, provided is a tulip as described herein wherein the tulip head is configured with a pinch point at the top of the upper chamber, and the pinch point is configured to press against the upper part of the saddle so that the two saddle horns are forced closer towards each other, thus keeping the fusion rod in place before fixation into a final position.

According to an embodiment of the present invention, provided is a tulip as described herein wherein an outside or upper rim part of the tulip head comprises docking area which are configured to allow a tulip assembly tool to securely grab the tulip head.

According to an embodiment of the present invention, provided is a tulip as described herein wherein the tulip head is made of a rigid material, and the tulip collet is made of a less rigid material.

According to an embodiment of the present invention, provided is a tulip as described herein wherein the tulip head is made of a rigid material including one or more of cobalt-chrome, cobalt-chrome alloy, titanium, titanium alloy, and the tulip collet is made of a less rigid material.

According to an embodiment of the present invention, provided is a tulip as described herein wherein the tulip head is made of one or more of cobalt-chrome, and cobalt-chrome alloy, optionally coated with one or more of titanium and titanium alloy, and the tulip collet is made of one or more of titanium and titanium alloy.

According to an embodiment of the present invention, provided is a system for connecting a fusion rod to a poly axial screw, the system comprising a tulip head, a tulip collet, and a screw shaft with ball head, wherein the poly axial screw shaft is configured for implantation without the tulip; wherein the collet is configured with an upper saddle part with a base and two saddle horns and a lower jaw joint part; wherein the saddle, its base and its two saddle horns are configured to connect to a fusion rod, with the length of the rod sitting across the saddle base, the two horns cradling part of the sides of the rod; wherein the jaw joint is configured with an open and a closed position, and comprises a plurality of jaw joint members that are configured to be separated in the open position, and to make closer contact with each other in the closed position; wherein the tulip head comprises two chambers, an upper chamber and a lower chamber; wherein the upper chamber is wider than the lower chamber, and the upper chamber is configured to loosely fit the ball head of the poly axial screw shaft and the collet with its jaw joint in the open position; wherein the lower chamber is tighter than the upper chamber and the lower chamber is configured to tightly fit the collet with its jaw joint in the closed position around the ball head of the poly axial screw shaft and thus to lock the tulip in position while allowing it to rotate and pivot against the ball head upon actuation of manual force; wherein the top part of the tulip head is configured to engage with a fastener to allow fixation of the connection to a fusion rod in its final position.

According to an embodiment of the present invention, provided is a system comprising a tulip head, tulip collet and screw shaft with ball head as described herein, additionally comprising a fusion rod.

According to an embodiment of the present invention, provided is a system as described herein, wherein the tulip head is configured with a pinch point at the top of the upper chamber, and the pinch point is configured to press against the upper part of the saddle so that the two saddle horns are forced closer towards each other, thus keeping the fusion rod in place before final fixation with a set screw.

According to an embodiment of the present invention, provided is a system as described herein, wherein an outside or upper rim part of the tulip head comprises a docking area that is configured to allow a tulip assembly tool to securely grab the head.

According to an embodiment of the present invention, provided is a system as described herein, wherein the tulip head is made of a rigid material, and the tulip collet is made of a less rigid material.

According to an embodiment of the present invention, provided is a system as described herein, wherein the tulip head is made of a rigid material including one or more of cobalt-chrome, cobalt-chrome alloy, titanium, titanium alloy, and the tulip collet is made of a less rigid material.

According to an embodiment of the present invention, provided is a system as described herein, wherein the tulip head is made of one or more of cobalt-chrome, and cobalt-chrome alloy, optionally coated with one or more of titanium and titanium alloy, and the tulip collet is made of one or more of titanium and titanium alloy.

According to an embodiment of the present invention, provided is a method of assembly of a poly axial screw from a tulip head and tulip collet onto an implanted screw shaft during spinal fusion surgery; wherein the collet is configured with an upper saddle part and a lower jaw joint part, and the jaw joint is configured with an open and a closed position, and comprises a plurality of jaw joint members that are configured to be separated in the open position, and to make closer contact with each other in the closed position; wherein the tulip head comprises an upper chamber and a lower chamber, and the upper chamber is wider than the lower chamber and is configured to loosely fit around the ball head of the poly axial screw shaft and the collet with its jaw joint in the open position; wherein the lower chamber is tighter than the upper chamber and is configured to tightly fit the collet with its jaw joint in a closed position around the ball head of the poly axial screw shaft and thus to lock the tulip in position while allowing it to rotate and pivot against the ball head upon actuation of manual force; wherein the method comprising the steps of: implanting the screw shaft with ball head into a bone, including the pedicle of a vertebrae; and assembling the tulip head and collet onto the ball head by actuating a downward force upon the top of the tulip collet, thus moving the collet into a lower chamber of the tulip head, the walls of the tighter lower chamber thus squeezing the jaw joint members circumferentially onto the ball head thereby achieving a locked position that remains rotatably and pivotably adjustable by manual force.

According to an embodiment of the present invention, provided is a method as described herein, wherein a fusion rod is inserted into the collet saddle and a fastener is partially tightened until the collet is moved completely into a lower tighter chamber of the tulip head, thus squeezing the jaw joint members circumferentially onto the ball head and thereby achieving a locked position that remains adjustable by manual force.

According to an embodiment of the present invention, provided is a method as described herein, wherein a tulip assembly tool is used, and wherein an outside or upper rim part of the tulip head is configured with a docking area to allow the tulip assembly tool to securely grab the tulip head; wherein the tulip assembly tool comprises outer hooks that are configured to engage the docking area of the tulip head, and comprises a center dowel that is configured to engage the top of the tulip collet when the collet is placed in the upper chamber of the tulip head, and is configured to push down onto the collet thereby moving the collet into the lower chamber of the tulip head when the tool is actuated; wherein the method comprising the steps of: implanting the screw shaft with ball head into a bone, including the pedicle of a vertebrae; assembling the tulip head and collet onto the ball head; positioning the tulip assembly tool so that the hooks of the tool make contact with the docking area of the tulip head; and actuating the tool thus applying a downward force upon the tulip collet, thus forcing the collet into the lower chamber of the tulip head, the walls of the tighter lower chamber squeezing the jaw joint members circumferentially onto the ball head thereby achieving a locked position that remains adjustable by manual force.

According to an embodiment of the present invention, provided is a tulip assembly tool for assembly of a tulip head and tulip collet with collet jaw joint onto the ball head of a poly axial screw shaft during spinal fusion surgery, wherein the tool comprises outer hooks that are configured to engage a matching docking area on the outside or upper rim part of the tulip head; wherein the tool comprises a center dowel that is configured to engage a top of the tulip collet when the collet is placed in an upper chamber of the tulip head; wherein the tool is configured to push down onto the collet with its center dowel and move the collet downwards a sufficient distance to reach a lower tighter chamber of the tulip head for the jaw joint of the collet to engage and close around the ball head of the poly axial screw shaft thus achieving a locked position that remains adjustable by manual force.

The foregoing summary of the present invention with the preferred embodiments should not be construed to limit the scope of the invention. It should be understood and obvious to one skilled in the art that the embodiments of the invention thus described may be further modified without departing from the spirit and scope of the invention. Other features and advantages of the invention will be apparent from the following specification taken in conjunction with the following drawings. While many materials and methods of design have been attempted, a number of drawback and limitations prevent an optimal design.

BRIEF DESCRIPTION OF THE DRAWINGS

FIG. 3 is a sectional view of a pre-assembly poly axial screw with screw shaft, ball head and tulip head, in accordance with an embodiment of the present invention;

FIG. 4 is a sectional view of a poly axial screw in mid-assembly, with assembled tulip head and a pre-assembly tulip collet, in accordance with an embodiment of the present invention; and FIG. 5 is a sectional view of a poly axial screw with assembled tulip collet before locking connection, in accordance with an embodiment of the present invention.

FIG. 6 is a sectional view of poly axial screw with tulip after locking connection, in accordance with an embodiment of the present invention.

FIG. 7 is a sectional view of a poly axial screw with inserted fusion rod, in accordance with an embodiment of the present invention.

FIG. 8 is a sectional view of a poly axial screw with inserted fusion rod secured by a set screw, in accordance with an embodiment of the present invention.

DETAILED DESCRIPTION

The present invention generally relates to connectors that connect poly axial screws with fusion rods for use in spinal fusion surgery, and to poly axial screw systems comprising such connectors. In particular, the present invention relates to poly axial screw systems configured to provide an adjustably locked preliminary, and a fixated final position for the tulip with fusion rod.

Figure 1:
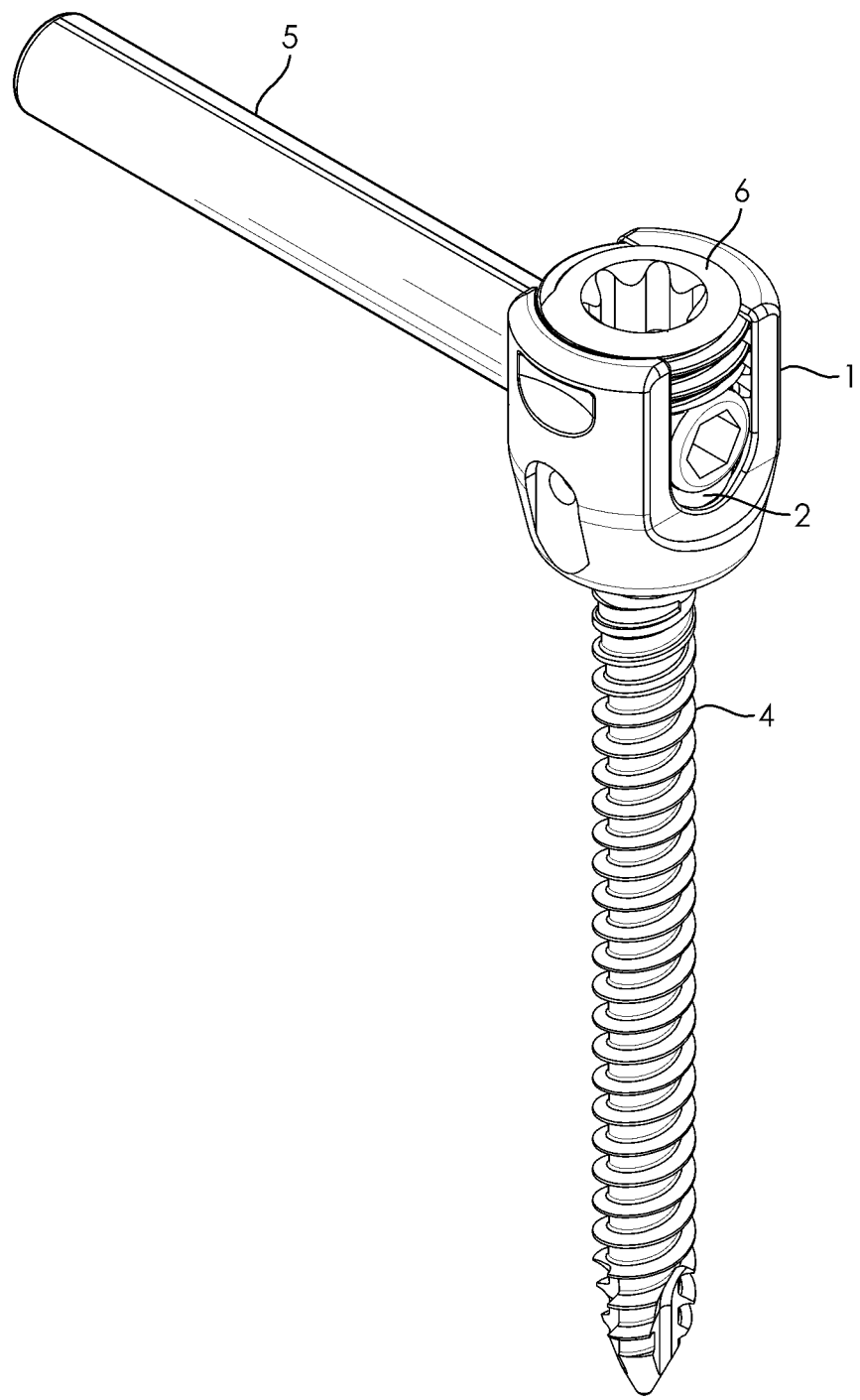
FIG. 1 is a perspective view of an assembled poly axial screw connected to a fusion rod, in accordance with an embodiment of the present invention.

The poly axial screw system of the present invention is configured for assembly during surgery, after implantation of the screw shaft (see FIG. 1). The system comprises a two-part tulip connector with a head and a collet (see FIG. 2) that is configured to lock into a rotatable and pivotable position onto the ball head of the implanted screw shaft, with the locked position remaining adjustable by manual force. The tulip may be locked by partially tightening a set screw, or by using a tulip assembly tool configured to hook onto the tulip head with its outer hooks and press down onto the tulip collet with its center dowel. The system can then be fixated into a final position by completely tightening the set screw.

In embodiments of the invention, the tulip head and collet are configured with a loose and a locked position when engaging with each other and with the ball head or the screw shaft during assembly of the poly axial screw system. In the loose position, the tulip loosely fits onto the ball head of an implanted screw shaft. In the locked position, the tulip tightly fits around the ball head, providing sufficient rigidity and stability to reliably keep the position the tulip is placed in during surgery (safeguarding against the occasional inadvertent touch or bump by the surgeon's hands, tools, moving tissue, bone structure, implants etc.), while remaining pivotably and rotatably adjustable by manual force. After all adjustments have been made, the poly axial screw system can be fixated into a final position using a fastener, typically a set screw, cap or similar.

In embodiments of the invention, the tulip may comprise two separate parts, a two-chambered tulip head and a tulip collet which has an open and a closed position that match the dimensions of the tulip head's upper and lower chamber, respectively, to lock the tulip in place when the collet is pushed down into the lower chamber and thus squeezed into its closed position by the walls of the tighter lower chamber (see FIGS. 3 and 4). This configuration may avoid excessive torque during preliminary adjustments, both when the set screw method of assembly is used (which pushes the collet down into the lower chamber of the tulip head by partial light tightening of the screw, avoiding over-tightening and providing a defined degree of rigidity), and also when the tulip assembly tool is used (which pushes down rather than rotates, thus avoiding torque).

According to an embodiment of the present invention, the collet may be configured with an upper section or saddle and a lower section or jaw joint.

The saddle of the collet has a base and two saddle horns, and is configured to accept the fusion rod sitting across the base and in between its two saddle horns after the collet is locked onto the ball head of the screw shaft (see FIG. 5).

In embodiments of the invention, the jaw joint of the collet may be configured with an open and a closed position. In the open position, the jaw joint is configured to accept the ball head of the screw shaft in a loose fit. In the closed position, a tight fit is achieved in which the ball head can still rotatably and pivotably move inside the jaw joint, thus providing sufficient stability but allowing micro-adjustment of position.

Figure 2:
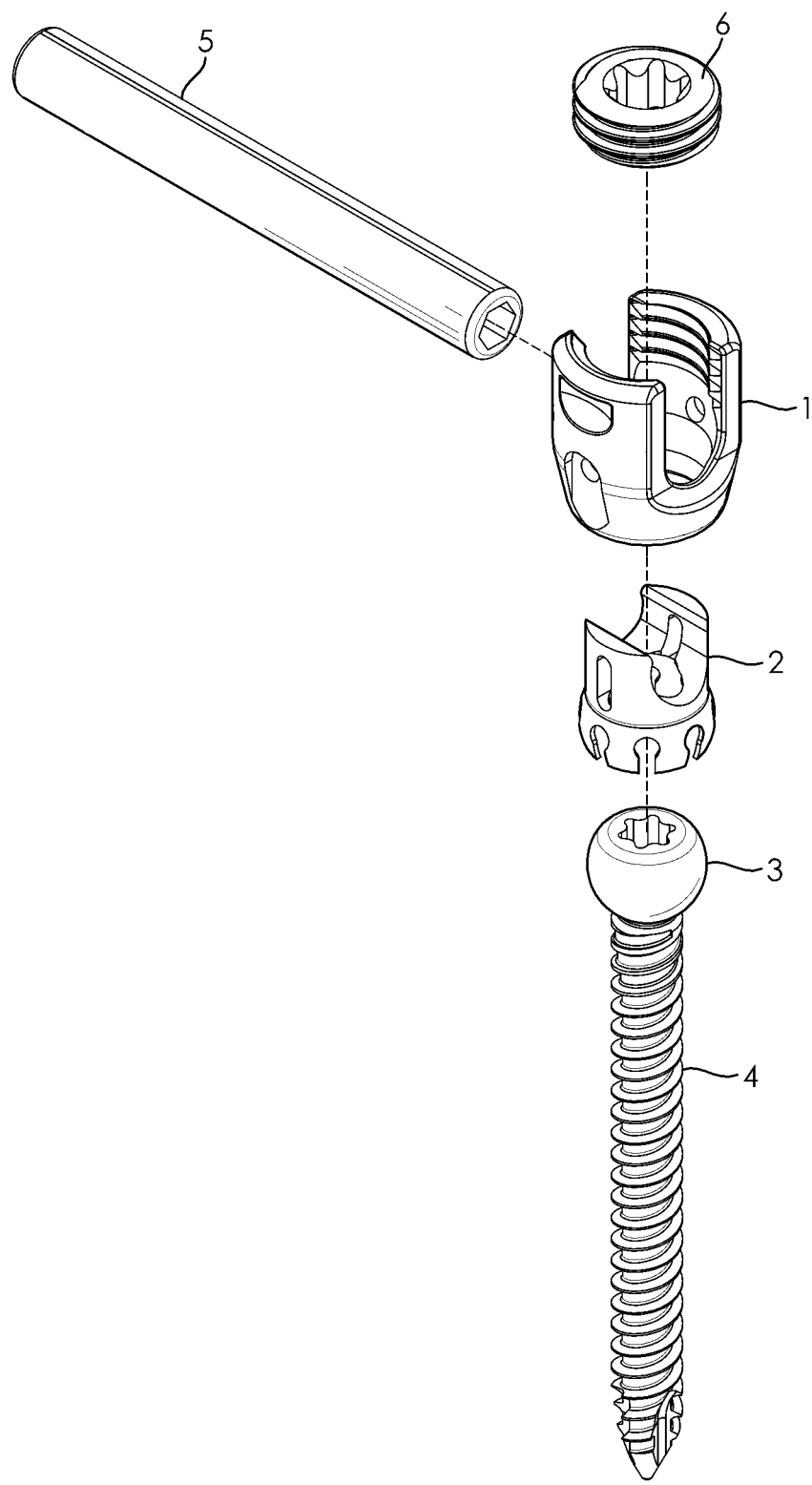
FIG. 2 is an exploded perspective view of an assembled poly axial screw connected to a fusion rod, in accordance with an embodiment of the present invention.

In embodiments of the invention, the jaw joint may be configured with a plurality of members that are aligned to follow the dimensions of the outer contours of the ball head, to loosely cradle it in the open position, and to tightly fit around the ball head when pushed together in the closed position, see e.g. FIG. 2-4 for an illustrative example of an appropriate shape for the jam joint members. The jaw joint members may have any shape that allows them to cradle/loosely fit the ball head in an open position, and to move closer together and tightly fit in a closed position. Generally the jaw joint members are separate, and may number from 2 to 10 or more members, for example, 6-8 members. However, depending on the material, if a flexible/stretchable material is used, or one or more material of different thickness, the jaw joint members may be joined to each other fully or partially in an expanded/open position, and a contracted/closed position may be achieved by the material being pushed together and contracted, e.g. on predetermined folding lines or due to flex.

The ball head of the screw shaft may have a substantially spherical shape, and may be spherical, oval or ellipsoid, and optionally may have a flattened top. The tulip head and collet match the shape of the ball head to provide a loose or tight fit in the open or closed positions, respectively, as described herein-below.

According to an embodiment of the present invention, the tulip head may be configured to accommodate the collet in an open position in which the collet and head provide a loose fit around the ball head, and to facilitate transformation into a locked position in which the collet and head provide a tight fit around the ball head. Further the tulip head may be configured with a means to fixate the fusion rod into the final position.

In embodiments of the invention, the tulip head may be configured with two inner chambers: an upper chamber and a lower chamber to provide a loose and a locked position, with an optional pinch point to provisionally hold the fusion rod in place before fixation, and a threaded top section to achieve fixation into the final position using a set screw.

In embodiments of the invention, the upper chamber may configured to accommodate the ball head with the collet in an open configuration, in particular, with the joint jaw in the open position. The lower chamber may be configured to provide a tighter fit and may be configured to fit the ball head with collet joint jaw in the closed position only. Thus, the tulip head may be configured to fit over and loosely cradle the ball head of the screw shaft in the upper chamber. As the collet is pushed downwards into the lower or second chamber of the tulip head by the fusion rod and/or set screw, manually or by the tulip assembly tool, the walls of the tighter lower chamber push the collet jaw joint members closed into the rotatable and pivotable locked position.

In embodiments of the invention, the upper chamber of the tulip head may be configured with a pinch point. As the collet is pushed downwards when moving into the locked position, the pinch point pushes the two horns of the upper saddle together slightly, so that when the rod is inserted, it is kept in place (see FIG. 5).

In embodiments of the invention, the fusion rod may be inserted into and held in place by the collet. In particular, the length of the fusion rod may sit across the saddle base and its sides may be stabilized by the saddle horns of the collet. A pinch point in the tulip head may be configured to sit near the top of the inserted fusion rod after the tulip is in its locked position. For example, the pinch point may be configured in the wall of the upper chamber of the tulip head, in particular, near the top of the upper chamber of the tulip head. Thus, with the collet moved down and locked in closed position, and the fusion rod inserted, the pinch point will sit near the top of the fusion rod, so that as the fusion rod expands the saddle, the pinch point pushes the saddle horns inwards slightly around the rod to provisionally hold it in place before fixation.

According to an embodiment of the invention, the upper part of the tulip may be configured with a docking area to allow the tulip assembly tool to grab the tulip head during assembly of the tulip onto the ball head and for achieving the closed position. The docking area may be at the outer sides or upper rim of the tulip head, and may be configured as cutouts, protrusions or a rough surface area that matches the outer hooks of the tulip assembly tool and/or allows it to grab the tulip head by providing sufficient friction for a secure hold. The docking area cutouts or protrusions may have any suitable shape that fits correspondingly shaped hooks in the assembly tool. For example, slots or holes to fit the contacting hook area that may be line or pin shaped. Any matching configurations that allow the hooks to securely grab the docking area may be used, as will be apparent to a person of ordinary skill in the art.

Fasteners to achieve a final fixated position of the poly axial screw and the fusion rod typically comprise a set screw or cap and corresponding threaded top section of the tulip head for fastening. The threaded top may be an internal thread as shown in FIG. 1-6, or may be an external thread to match the internal thread of a cap. However, alternative fasteners may be used, and the poly axial screw system may be configured accordingly, for example for fixation with any suitable fastener that is of a biocompatible material and sufficient durability, including e.g. bolt and nut, rivet, latches, hooks, expanding anchors, or biocompatible adhesives, as will be apparent to a person skilled in the art.

If a set screw is used as a fastener, its screw head may be flat for a low profile, or it may be oval, pan, truss, round, or hex, and configured for suitable drive type accordingly, e.g. Phillips, slotted, combination, hex, torx, or square.

According to embodiments of the invention, the poly axial screw system may be assembled with or without a specialized tool.

Without specialized tool, in embodiments of the invention, the poly axial screw may be assembled from its system components simply by inserting the fusion rod and partially tightening the set screw, or by using any tool small enough to fit inside the tulip head and rigid enough to push down onto the top part of the collet. For example, the rod and set screw may be inserted, and the partial tightening of the set screw creates a downward force onto the rod and thus also the collet below. In certain embodiments of the invention, the collet may be pushed downwards into a second tighter chamber of the tulip head, thus achieving the locked position as described above.

Alternatively, in embodiments of the invention, the poly axial screw system may be assembled by using the tulip assembly tool described herein-below in detail. Use of the tulip assembly tool has the advantage that the tulip can be locked into a preliminary position even before the fusion rod is inserted, but remains adjustable manually even after insertion of the fusion rod.

According to an embodiment of the invention, the tulip assembly tool may be configured to securely grab the tulip head while pushing the tulip collet downwards a sufficient distance and with sufficient force to transform it into its closed position, thus locking the tulip onto the ball head. For example, the tool may be configured to move the collet from the upper chamber of the tulip head into the tighter lower chamber, and to cause the collet jaw joint members to be squeezed circumferentially onto the ball head by the downward force of the tool and the walls of the tighter lower chamber of the tulip head.

In embodiments of the invention, the tulip assembly tool may comprise an outer hook and a center dowel. The outer hook is configured to grab the docking area of the tulip head, and the center dowel is configured to make contact with the collet of the tulip inserted in the upper chamber of the tulip, and is configured to allow the collet to be pushed downwards a sufficient distance and with sufficient force to move into the second chamber, and thus into the locked position.

In embodiments of the invention, the tulip assembly tool may be made from metal, sufficiently rigid polymers, carbon fiber, or a combination thereof, and may comprise areas where the surface is textured or coated, e.g. with rubber or a similar softer material, to increase friction. For example, the tool may be stainless steel and may have crisscrossing grooves at one or more areas where outer hooks and center dowel make contact with the tulip head and tulip collet, respectively, and optionally rubber pads or coatings.

According to an embodiment of the invention, in the method with tulip assembly tool, the tool is placed onto the tulip head so that it securely grabs it, and is actuated so that it moves the tulip into the locked position. For example, the tool may move the collet downwards to achieve the locked position. In particular, the tool may move the collet downwards into a tighter lower chamber with the walls and the downward force squeezing the collet jaw joint into a closed position around the ball head of the screw shaft. For example, the tool may be configured with a center dowel that moves downward, e.g. by manual pressure, or by actuating the tool electrically, for example by twisting its handle or activating an actuating part, for example a button, slider, switch or similar, as will be apparent to a person of ordinary skill in the art.

The poly axial screw parts (tulip head, tulip collet, set screw and screw shaft with ball head) may be made from various biocompatible materials suitable for implantation into the mammalian or human body, including various metals, metal alloys and their mixtures, coated metals or coated metal alloys, polymers, and oxide ceramics, as will be apparent to a person of ordinary skill in the art. These may include, for example, stainless steel, pure titanium standard, titanium alloy, TAV (Ti6Al4V), TAN (Ti6AL7Nb), TAN standard (titanium-coated cobalt-chrome), TAN new finish (titanium-coated cobalt-chrome), cobalt-chrome, cobalt-chrome alloys, cobalt-chrome/titanium coating, cobalt-chrome/zirconium/titanium coating, cobalt-chrome-molybdane, zirconium, aluminum, vanadium, vitallium, plastic polymers such as ultra-high-molecular weight—polyethylene (UHMWP), polyetheretherketone (PEEK), polyurethanes and composites including composites containing carbon fiber, polycarbonate urethane, natural or synthetic elastomers such as polyisoprene (natural rubber), synthetic polymers, copolymers, and thermoplastic elastomers, for example, polyurethane elastomers such as polycarbonate-urethane elastomer, other polymers and oxide ceramics. Titanium and its alloys may be used for superior bone on-growth compared to other metals and metals/metal alloys.

The poly axial screw parts may be made from one material, or a combination of one or more different materials (including differently treated materials that have different characteristics). Different materials may be used to form any or all of the poly axial screw parts based upon the desired characteristics such as strength, hardness, rigidity, resilience and elasticity of the specific part. For example, the tulip head and set screw may be formed from cobalt-chrome, and the collet and screw shaft with ball head may be formed from titanium or a titanium alloy. If different metal or metal alloys are combined, especially when in direct contact, metal combinations that can promote corrosion should be avoided, or optionally suitable coatings may be used, as will be apparent to the person of ordinary skill in the art.

The tulip collet is typically made from less rigid materials that are more easily deformable than the remaining poly axial screw parts (i.e. tulip head, set screw, and screw shaft with ball head).

The screw shaft is threaded, typically with a V-thread, but other thread types with different thread angles may be used, for example, buttress or square threads. The screw shaft and may optionally comprise additional features such as radial holes, depending on the particular application and patient, e.g. to increase pull-out strength, as will be apparent to a person of ordinary skill in the art. Optionally, the screw shaft may be cannulated, to allow a guide wire to pass through for placement, e.g. a fluorescent wire for imaging technique-assisted placement.

The poly axial screws parts optionally may be surface treated with various methods according to the material used, as will be apparent to a person of ordinary skill in the art. Surface treatment results in a rougher surface that typically promotes osseointegration. Various methods are known and may result in 0.05 µm-0.5 µm surface roughness, e.g. 0.15 µm-0.4 µm or 0.2 µm-0.35 µm. For example, a steel surface may be electropolished to a surface roughness of about 0.2 µm to about 0.24 µm, e.g. about 0.22 µm; a cobalt chrome surface may be treated by passivation to achieve the same surface roughness; a TAN surface may be prepared by electrochemical anodisation to a surface roughness of about 0.3 µm-0.34 µm, e.g. about 0.32 µm; and a TAN-new-finish may be additionally polished to a surface roughness of ca. 0.28 µm).

The embodiments of the present invention may be used in various types of bone-stabilizing surgery, including but not limited to spinal surgery, in particular spinal fusion surgery. For example, embodiments of the present invention may be useful for posterolateral fusion, interbody fusion, Posterior lumbar interbody fusion (PLIF, the disc is accessed from a posterior position and includes removing the disc between two vertebrae and inserting bone into the space created between the two vertebral bodies), Posterolateral gutter fusion (the procedure is done through the back), Anterior lumbar interbody fusion (ALIF, the disc is accessed from an anterior abdominal incision and includes removing the disc between two vertebrae and inserting bone into the space created between the two vertebral bodies), Anterior/posterior spinal fusion, Transforaminal lumbar interbody fusion (TLIF, the disc is accessed from a posterior incision on one side of the spine), Extreme Lateral Interbody Fusion (XLIF, an interbody fusion in which the disc is accessed laterally), Transpsoas interbody fusion (DLIF or XLIF, the disc is accessed from an incision through the psoas muscle on one side of the spine), and Oblique lateral lumbar interbody fusion (OLLIF, the disc is accessed from an incision through the psoas muscle obliquely).

Exemplary Embodiments

Turning to FIG. 1, a perspective view of an assembled poly axial screw connected to a fusion rod 5 is shown in accordance with an embodiment of the present invention. The use of the set-screw 6 to fixate the rod 5 in position is illustrated;

In FIG. 2, an exploded perspective view of an assembled poly axial screw connected to a fusion rod 5 is shown in accordance with an embodiment of the present invention. The components including (from bottom to top) screw shaft 4 with ball head 3, collet 2, tulip head 1 and set screw 6 are shown;

In FIG. 3, a sectional view of the screw shaft 4 with its ball head 3 and a pre-assembly tulip head 1 of a poly axial screw is shown, in accordance with an embodiment of the present invention;

In FIG. 4, a sectional view of a tulip head 1 assembled onto the ball head 3 of the screw shaft 4 of a poly axial screw and of a pre-assembly tulip collet 2 is shown, in accordance with an embodiment of the present invention. The illustration shows the collet 2, with its upper saddle part with a saddle base 8 and two saddle horns 7, and a lower jaw joint part. The collet 2 is shown in its open position, with its jaw joint members 9 fully separated;

In FIG. 5, a sectional view of a tulip (with its head 1 and its collet 2) assembled onto the ball head 3 of the screw shaft 4 of a poly axial screw is shown, in accordance with an embodiment of the present invention. The illustration shows the collet 2 in its open position with the jaw joint members 9 fitting loosely around the ball head 3 of the screw shaft 4 in the upper wider chamber of the tulip head 1;

In FIG. 6, a sectional view of a tulip after its locking connection to the ball head 3 of the screw shaft 4 of a poly axial screw is shown, in accordance with an embodiment of the present invention. The illustration shows the collet 2 in its closed position, after exertion of downwards pressure on the top of the collet 2 and side pressure from the walls of the lower tighter chamber of the tulip head 1, and with the jaw joint members 9 moved closer together to provide a tight fit around the ball head 3;

In FIG. 7, a sectional view of a poly axial screw with a locked-on tulip and a fusion rod 5 inserted into the tulip is shown, in accordance with an embodiment of the present invention. The illustration shows the fusion rod 5 contacting the saddle, sitting on top of the saddle base 8 and cradled between the two saddle horns 7. The pinch points at the top of the upper tulip chamber that press the top of the saddle horns of the collet slightly inwards/around the fusion rod are shown (inward movement not depicted); and In FIG. 8, a sectional view of a poly axial screw with a fusion rod 5 inserted into the tulip, and a set screw 6 securing the fusion rod in its position is shown, in accordance with an embodiment of the present invention.

While multiple embodiments are disclosed, still other embodiments of the present invention will become apparent to those skilled in the art from this detailed description. There may be aspects of this invention that may be practiced without the implementation of some features as they are described. It should be understood that some details have not been described in detail in order to not unnecessarily obscure focus of the invention. The invention is capable of myriad modifications in various obvious aspects, all without departing from the spirit and scope of the present invention. It should be noted that the features illustrated in the drawings are not necessarily drawn to scale, and features of one embodiment may be employed with other embodiments as the skilled artisan would recognize, even if not explicitly stated herein. Accordingly, the drawings and descriptions are to be regarded as illustrative in nature and not restrictive.

What is claimed is:

1. A tulip for connecting a fusion rod to a poly axial screw, the tulip comprising:
    a u-shaped tulip head with partially threaded side walls; and
    a collet configured for mounting onto a ball head of a poly axial screw during spinal fusion surgery, said collet being configured to fit through an opening in a base of said tulip head,
    wherein the collet includes:
        an upper saddle part with a base and two saddle horns; and
        a lower jaw joint part,
            wherein the saddle, its base and its two saddle horns are configured to receive a fusion rod, wherein the fusion rod sits across the saddle base and is cradled by the two horns,
            wherein each saddle horn defines an inwardly projecting, opposing lip along a top end thereof, wherein when said rod is seated in said collet said opposing lips project towards each other and flank the rod,
            wherein the jaw joint is configured to assume an open and a closed position, and comprises a plurality of jaw joint members that are configured to be separated in the open position, and converge in the closed position, wherein the jaw joint in its open position is configured to accept and fit loosely around the ball head of a poly axial screw, and in its closed position is configured to fit tightly around the ball head,
    wherein the tulip head comprises:
        an upper chamber; and
        a lower chamber,
            wherein the upper chamber is wider than the lower chamber, and the upper chamber is configured to loosely accommodate the ball head of the poly axial screw and the collet with its jaw joint in the open position,
            wherein the lower chamber is narrower than the upper chamber and the lower chamber is configured to fit tightly around the collet with its jaw joint in a closed position around the ball head of the poly axial screw, and thus to lock the tulip in position while allowing it to rotate and pivot against the ball head upon actuation of manual force;
    wherein the top part of the tulip head is configured to engage with a fastener, thus allowing fixation of the poly axial screw to the fusion rod in their final positions.

2. The tulip of claim 1, wherein the tulip head includes a pinch point at the top of the upper chamber, wherein the pinch point is configured to press against an upper part of the saddle so that the two saddle horns are forced closer towards each other, thereby causing the opposing lips of said saddle horns to converge, thus keeping the fusion rod in place before fixation into a final position.

3. The tulip of claim 2, wherein fixation into final position is accomplished by threading a set screw into the threaded portion of the tulip head until the fusion rod is squeezed between the set screw and the collet is pushed down into the lower chamber of the tulip head.

4. The tulip of claim 1, wherein an outside or upper rim part of the tulip head comprises docking area which are configured to allow a tulip assembly tool to securely grab the tulip head.

5. The tulip of claim 1, wherein the tulip head is made of a rigid material, and the tulip collet is made of a less rigid material.

6. A system for connecting a fusion rod to a poly axial screw, the system comprising:
   a u-shaped tulip head with partially threaded side walls;
   a tulip collet; and
   a poly axial screw with ball head,
   wherein the collet includes:
      an upper saddle part with a base and two saddle horns; and
      a lower jaw joint part,
         wherein the saddle, its base and its two saddle horns are configured to receive a fusion rod, wherein the fusion rod sits across the saddle base, and is cradled by the two horns,
         wherein the jaw joint is configured to assume an open and a closed position, and comprises a plurality of jaw joint members that are configured to be separated in the open position, and to make contact with each other in the closed position,
      wherein each saddle horn defines an inwardly projecting, opposing lip along a top end thereof, wherein when said rod is seated in said collet said opposing lips project towards each other and flank the rod;
   wherein the tulip head comprises:
      an upper chamber; and
      a lower chamber,
         wherein the upper chamber is wider than the lower chamber, and the upper chamber is configured to loosely accommodate the ball head of the poly axial screw and the collet with its jaw joint in the open position;
         wherein the lower chamber is narrower than the upper chamber and the lower chamber is configured to fit tightly around the collet with its jaw joint in the closed position around the ball head of the poly axial screw and thus to lock the tulip in position while allowing it to rotate and pivot against the ball head upon actuation of manual force;
   wherein the top part of the tulip head is configured to engage with a fastener to allow fixation of the connection to a fusion rod in its final position.

7. The system of claim 6, further comprising a fusion rod.

8. The system of claim 6, wherein the tulip head is configured with a pinch point at the top of the upper chamber, and the pinch point is configured to press against the upper part of the saddle so that the two saddle horns are forced closer towards each other, thus keeping the fusion rod in place before final fixation with a set screw.

9. The system of claim 6, wherein an outside or upper rim part of the tulip head comprises a docking area that is configured to allow a tulip assembly tool to securely grab the head.

10. The system of claim 6, wherein the tulip head is made of a rigid material including one or more of cobalt-chrome, cobalt-chrome alloy, titanium, titanium alloy, and the tulip collet is made of a less rigid material.

11. The system of claim 6, wherein the tulip head is made of one or more of cobalt-chrome, and cobalt-chrome alloy, optionally coated with one or more of titanium and titanium alloy, and the tulip collet is made of one or more of titanium and titanium alloy.

12. The system of claim 6, wherein the tulip head is made of a rigid material including one or more of cobalt-chrome, cobalt-chrome alloy, titanium, titanium alloy, and the tulip collet is made of a less rigid material.

13. The system of claim 6, wherein the tulip head is made of one or more of cobalt-chrome, and cobalt-chrome alloy, optionally coated with one or more of titanium and titanium alloy, and the tulip collet is made of one or more of titanium and titanium alloy.

14. The system of claim 6, wherein the tulip head is made of a rigid material including one or more of cobalt-chrome, cobalt-chrome alloy, titanium, titanium alloy, and the tulip collet is made of a less rigid material.

15. The system of claim 6, wherein the tulip head is made of one or more of cobalt-chrome, and cobalt-chrome alloy, optionally coated with one or more of titanium and titanium alloy, and the tulip collet is made of one or more of titanium and titanium alloy.

16. A method of assembly of a poly axial screw from a tulip head and tulip collet onto an implanted screw during spinal fusion surgery, the method comprising:
   implanting the screw into a bone, including the pedicle of a vertebrae; and
   mounting the tulip head and collet onto a ball head of the screw by actuating a downward force upon the top of the tulip collet, thus moving the collet into a lower chamber of the tulip head,
   wherein the collet includes:
      an upper saddle part having a base and two saddle horns; and
      a lower jaw joint part configured to assume an open and a closed position, and comprising a plurality of jaw joint members that are configured to be separated in the open position, and to make contact with each other in the closed position,
      wherein each saddle horn defines an inwardly projecting, opposing lip along a top end thereof,
      wherein when said rod is seated in said collet said opposing lips project towards each other and flank the rod;
   wherein the tulip head comprises an upper chamber and a lower chamber,
      wherein the upper chamber is wider than the lower chamber, and the tulip head is configured to loosely accommodate a ball head of the poly axial screw and the collet with its jaw joint in the open position,
      wherein the lower chamber is narrower than the upper chamber and is configured to fit tightly around the collet with its jaw joint in a closed position around the ball head of the poly axial screw and thus to lock the tulip in position while allowing it to rotate and pivot against the ball head upon actuation of manual force;
      wherein when the collet is moved into the lower chamber of the tulip head the walls of the narrower lower chamber squeeze the jaw joint members circumferentially onto the ball head thereby achieving a locked position that remains rotatably and pivotably adjustable by manual force.

17. The method of claim 16, wherein a fusion rod is inserted into the collet saddle and a fastener is partially tightened until the collet is moved completely into a lower tighter chamber of the tulip head, thus squeezing the jaw joint members circumferentially onto the ball head and thereby achieving a locked position that remains adjustable by manual force.

18. The method of claim 16, wherein a tulip assembly tool is used, and wherein an outside or upper rim part of the tulip head is configured with a docking area to allow the tulip assembly tool to securely grab the tulip head;
  wherein the tulip assembly tool comprises outer hooks that are configured to engage the docking area of the tulip head, and comprises a center dowel that is configured to engage the top of the tulip collet when the collet is placed in the upper chamber of the tulip head, and is configured to push down onto the collet thereby moving the collet into the lower chamber of the tulip head when the tool is actuated;
  wherein the method comprising the steps of:
    implanting the screw with ball head into a bone, including the pedicle of a vertebrae;
    assembling the tulip head and collet onto the ball head;
    positioning the tulip assembly tool so that the hooks of the tool make contact with the docking area of the tulip head; and
    actuating the tool thus applying a downward force upon the tulip collet, thus forcing the collet into the lower chamber of the tulip head, the walls of the tighter lower chamber squeezing the jaw joint members circumferentially onto the ball head thereby achieving a locked position that remains adjustable by manual force.

* * * * *